United States Patent [19]

Chiaramonte

[11] 4,402,716
[45] Sep. 6, 1983

[54] WEARABLE VACUUM PROTECTIVE DEVICE

[76] Inventor: Vincent Chiaramonte, 75 Farmers Ave., Lindenhurst, N.Y. 11757

[21] Appl. No.: 336,564

[22] Filed: Jan. 4, 1982

Related U.S. Application Data

[63] Continuation-in-part of Ser. No. 187,356, Sep. 15, 1980, abandoned.

[51] Int. Cl.³ .................. B01D 46/10; B24B 55/00
[52] U.S. Cl. ......................... 55/356; 55/471; 55/493; 51/270; 51/273
[58] Field of Search ............ 55/356, 385 R, 471, 55/493, 503, DIG. 18, DIG. 33, DIG. 35; 422/120; 128/202.26, 205.22; 51/270, 273

[56] References Cited

U.S. PATENT DOCUMENTS

| | | | |
|---|---|---|---|
| 2,575,483 | 11/1951 | Bethig | 55/316 |
| 3,496,703 | 2/1970 | MacLeod et al. | 55/356 |
| 4,054,132 | 10/1977 | Deeds | 128/205.22 |
| 4,292,061 | 9/1981 | Land | 55/493 |

FOREIGN PATENT DOCUMENTS 917117 12/1946 France .................. 55/471

Primary Examiner—David L. Lacey
Attorney, Agent, or Firm—James P. Malone

[57] ABSTRACT

A wearable vacuum protective device comprising a hollow bowl shape housing having a vacuum fan and a removable filter. An adjustable strap is connected to the housing, the strap being arranged to fit around the neck of the user to hold the housing against the user's chest.

3 Claims, 3 Drawing Figures

0
WEARABLE VACUUM PROTECTIVE DEVICE

This Application, is a continuation-in-part of Ser. No. 187,356, filed Sept. 15, 1980, now abandoned.

TECHNICAL FIELD

This invention relates to wearable vacuum protective devices and more particularly to such devices for use while performing grinding on a grinding wheel.

BACKGROUND ART

Many workers, for instance, dental technicians and dentists do a considerable amount of grinding in the making and fitting of dentures, bridges, crowns, etc. This grinding produces quantities of very fine metal and ceramic dust which if inhaled, are a health hazard to the user.

Bench mounted grinding wheels propel the dust directly at the operator and it is not convenient to have a vacuum device or blower located between the grinding wheel and the operator. This is not convenient since the operator has to look closely at the work pieces being ground. Also, much grinding is done by using a hand held grinding wheel, for instance, by dentists, which provides the same problem. The conventional practice is for the user to use a mask, however this is generally not too convenient.

THE INVENTION

The present invention provides a wearable vacuum protective device which is worn on the chest of the user. The vacuum device has a removable filter which will trap the dust coming off the grinding wheel. The vacuum protective device is mounted on adjustable straps arranged to fit around the neck and/or body of the user.

Accordingly, a principal object of the invention is to provide a new and improved wearable vacuum protective device.

Another object of the invention is to provide a new and improved wearable vacuum protective device for grinding wheel operators.

Another object of the invention is to provide new and improved wearable vacuum protective device comprising: a hollow bowl shape housing, a vacuum fan mounted in the housing, a removable filter mounted in the housing and an adjustable strap connected to the housing, the strap being arranged to fit around the neck of the user to hold the housing against the user's chest.

BRIEF DESCRIPTION OF THE DRAWINGS

These and other objects of the invention will be apparent from the following specification and drawings of which.

BEST MODE FOR CARRYING OUT THE INVENTION

Figure 1:
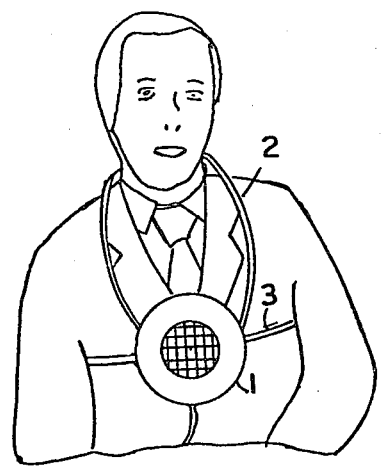
FIG. 1 is a diagram illustrating the use of the invention.
Figure 2:
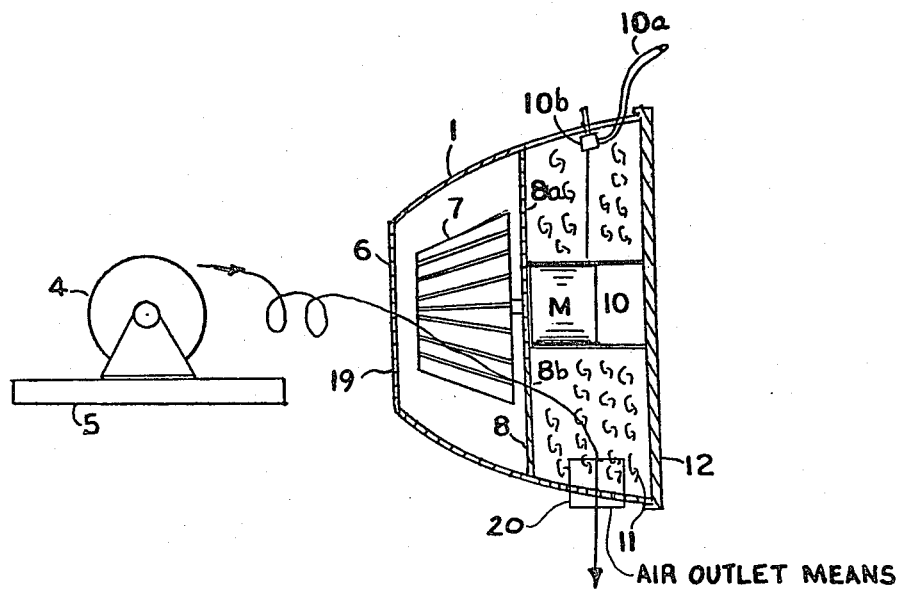
FIGS. 2 and 3 are side views partly in section illustrating the embodiments of the invention.

Referring to the drawings, FIGS. 1 and 2, the invention comprises a bowl shaped housing 1 having air inlet means 19 and air outlet means 20, which is mounted on the chest of the user by means of adjustable straps 2, which are arranged to fit around the neck of the user. An additional adjustable strap 3 may also be used to fit around the body of the user. The fine dust from the grinding wheel 4, mounted on the bench 5, is drawn into the vacuum housing 1 through the air inlet means 19. The air passes out the side of the housing 1 as shown by the arrow through the air outlet means 20 and the dust is trapped in a removable filter as will be explained.

Referring to FIG. 2, the housing 1 is bowl shaped having a larger diameter about eight inches, the small diameter about five inches, and a depth of about four inches. The front of the bowl has an open screen 6 covering the air inlet means 19. Behind the screen 6, a fan 7 is mounted on the partition 8, which is connected to the housing. The fan may comprise a series of turbine type blades. The partition 8 has a plurality of apertues 8a, 8b. A motor 10 is mounted on the partition 8 and is adapted to rotate the fan 7. The motor may be a conventional light weight motor of about 1/20 horsepower and may be a 110 volt motor which is connected directly into the house supply by means of the wire 10a and switch 10b. Alternatively, the motor could be a lower voltage motor, this however would require a separate power supply, preferably with a speed control.

A removable filter 11 is mounted around the motor and held in place by a removable cover 12. The filter may be made of any conventional filter material such as loosely packed cotton or other similar filter material. The entire assembly may be very light weight in weight and weigh about two or two and one-half pounds. The bowl housing and the fan blades may be of light weight plastic and the motor be a very small light weight motor.

When using the device, it is hung around the neck by means of the adjustable straps 2, which will normally be sufficient. If desired, the additional strap 3 may be strapped around the user's body. The device is then plugged in or otherwise switched on. When grinding operations are taking place, the dust laden air will be drawn in through the screen 6 and the air inlet means 19 and through the apertures in the partition 8, and the dust will be trapped by the filter. The filter may be removed and replaced periodically. The filter will serve to trap the fine metal, ceramics and glass dust which may contain poisonous elements such as uranium oxide.

Figure 3:
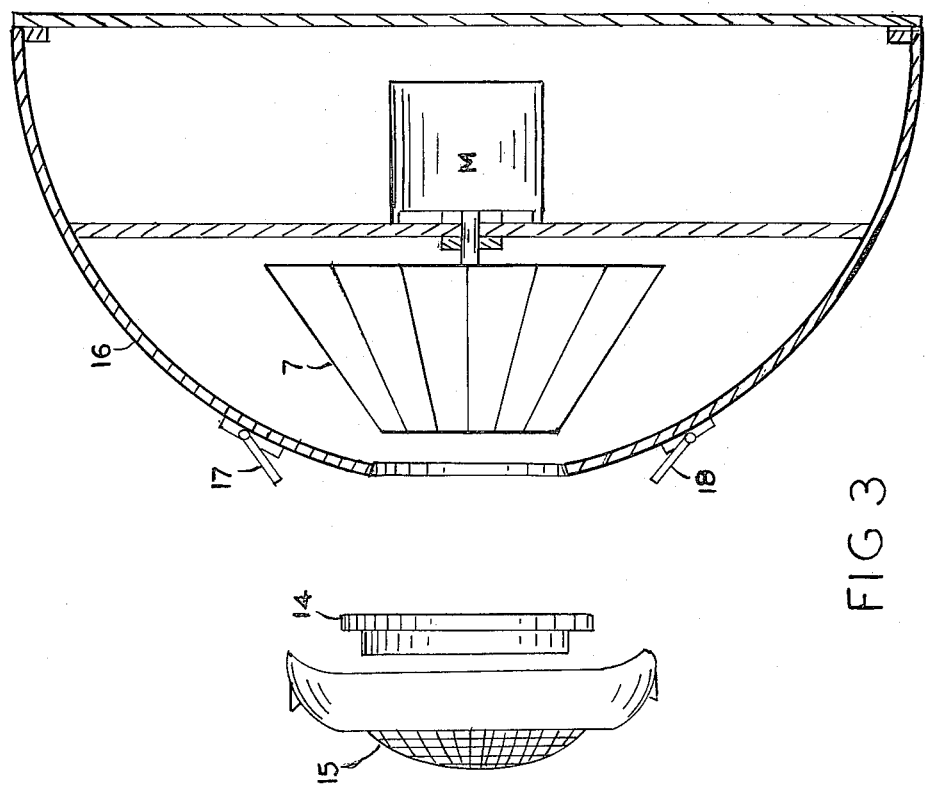

FIG. 3 shows another embodiment of the invention in which the filter 14 is mounted in front of the device and held in place by the removable screen 15 which is removably clamped on to the housing 16 by means of the fasteners 17, 18. The fan 7 and the motor are the same as shown in FIG. 2.

The vacuum fan is designed to run silently and to deflect particles away from the user's eyes, nose and mouth. Air enters through the screen 15 and passes out through the air outlet means as described in connection with FIG. 2.

It is claimed:

1. A light weight vacuum protective device having a size and weight to be wearable directly on the chest of the user of a grinding wheel in proximity to the grinding wheel, leaving no obstruction on the face of the individual leaving him free to see and talk readily comprising:
a hollow bowl shape housing shaped and sized to allow the user movement and comfort while grinding in either a sitting or standing position and having air inlet means and air outlet means,
a vacuum fan mounted in the housing designed to run silently and fast enough to deflect particles away from the user's eyes, nose and mouth and into the air inlet means and out the air outlet means, a removable filter mounted on the housing, so as to filter the air and so as to be easily removed and discarded along with the debris so that a new filter can be easily substituted, an adjustable first strap connected to the housing, the strap being arranged to fit around the neck of the user, to raise or lower the vacuum device thereby locating the device in such a way as to prevent the particles from reaching the user's face, a second adjustable strap connected to the housing and arranged to fit around the body of the user, to hold the housing against the user's chest.

2. Device as in claim 1 further including a removable screen and means for securing the screen to the housing so as to hold the filter on the housing.

3. Device as in claim 2 wherein said securing means comprises snap type fasteners.

* * * * *